United States Patent [19]
Ohki et al.

[11] Patent Number: 5,996,577
[45] Date of Patent: Dec. 7, 1999

[54] MEDICINE ADMINISTERING APPARATUS

[75] Inventors: Hisatomo Ohki; Shigemi Nakamura, both of Isesaki; Kazunori Ishizeki, Fujimi; Akira Yanagawa, Yokohama, all of Japan

[73] Assignees: Unisia Jecs Corporation, Atsugi; Dott Limited Company, Yokohama, both of Japan

[21] Appl. No.: 08/694,753

[22] Filed: Aug. 9, 1996

[30] Foreign Application Priority Data

Aug. 11, 1995 [JP] Japan ................................. 7-227266

[51] Int. Cl.⁶ ..................... A61M 15/00; A61M 16/00; B05D 7/14; B65D 83/06
[52] U.S. Cl. .............................. 128/203.15; 128/203.12
[58] Field of Search ................... 128/200.24, 203.12, 128/203.15, 203.21; 604/58

[56] References Cited

U.S. PATENT DOCUMENTS

| | | | |
|---|---|---|---|
| 2,581,182 | 1/1952 | Fields | 128/203.15 |
| 2,587,215 | 2/1952 | Priestly | 128/206 |
| 4,524,769 | 6/1985 | Wetterlin | 128/203.15 |
| 4,696,356 | 9/1987 | Ellion et al. | 177/123 |
| 4,811,869 | 3/1989 | Tremblay | 222/440 |
| 5,009,534 | 4/1991 | Gueret | 401/75 |
| 5,239,993 | 8/1993 | Evans | 128/203.15 |
| 5,320,714 | 6/1994 | Brendel | 128/203.15 |
| 5,327,883 | 7/1994 | Williams et al. | 128/203.15 |
| 5,331,953 | 7/1994 | Andersson et al. | 128/200.14 |
| 5,349,947 | 9/1994 | Newhouse et al. | 128/203.15 |

(List continued on next page.)

FOREIGN PATENT DOCUMENTS

| | | |
|---|---|---|
| 0 333 334 | 9/1989 | European Pat. Off. . |
| 0 640 354 A2 | 3/1995 | European Pat. Off. . |
| 4027391 | 12/1992 | Germany ................ 128/203.15 |
| 59-88158 | 5/1984 | Japan . |
| 1-47190 | 10/1989 | Japan . |
| 3-504457 | 10/1991 | Japan . |
| 2 165 159 | 4/1986 | United Kingdom . |
| WO 91/12040 | 8/1991 | WIPO ..................... 128/203.15 |
| 94/06498 | 3/1994 | WIPO . |
| 94/19041 | 9/1994 | WIPO . |
| 95/05208 | 2/1995 | WIPO . |

OTHER PUBLICATIONS

U.S. application No. 08/727,633, filed Nov. 1, 1996, Ohki et al.

U.S. application No. 08/823,314, filed Mar. 21, 1997, Ohki et al.

*Primary Examiner*—John G. Weiss
*Assistant Examiner*—Joseph F. Weiss, Jr.
*Attorney, Agent, or Firm*—Foley & Lardner

[57] ABSTRACT

A medicine administering apparatus, suitable for administering granular medicine to a patient, comprises a main body which has a medicine passage and a medicine accommodating chamber. The apparatus further includes a location changing member formed with a medicine loading chamber. The location of the medicine loading chamber is changed between a first position, where the medicine loading chamber is separate from the medicine passage, and a second position, where the medicine loading chamber is in the medicine passage. Movement of the location changing member changes the position of the medicine loading chamber. A medicine loading member compresses a predetermined amount of the medicine into the medicine loading chamber at the first position, the predetermined amount corresponding to one dose. Medicine within the medicine loading chamber may be inhaled through the medicine passage by a patient when the patient breathes in.

12 Claims, 8 Drawing Sheets

U.S. PATENT DOCUMENTS

| | | | |
|---|---|---|---|
| 5,429,122 | 7/1995 | Zanen et al. | 128/203.15 |
| 5,447,151 | 9/1995 | Bruna et al. | 128/203.15 |
| 5,505,196 | 4/1996 | Herold et al. | 128/203.15 |
| 5,546,932 | 8/1996 | Galli | 128/203.15 |
| 5,619,985 | 4/1997 | Ohki et al. | 128/203.21 |
| 5,634,900 | 6/1997 | Makino et al. | 128/203.15 |
| 5,647,349 | 7/1997 | Ohki et al. | 128/203.15 |
| 5,678,538 | 10/1997 | Drought | 128/203.15 |
| 5,715,811 | 2/1998 | Ohki et al. | 128/203.21 |
| 5,743,251 | 4/1998 | Howell et al. | 128/200.14 |
| 5,752,505 | 5/1998 | Ohki et al. | 128/203.15 |
| 5,810,004 | 9/1998 | Ohki et al. | 128/203.15 |
| 5,899,202 | 5/1999 | Ohki et al. | 128/203.22 |
| 5,901,703 | 5/1999 | Ohki et al. | 128/203.12 |

MEDICINE ADMINISTERING APPARATUS

BACKGROUND OF THE INVENTION

1. Field of the Invention

This invention relates to improvements in a medicine administering apparatus suitable for administering, for example, powder-like and granular medicine to a patient.

2. Description of the Prior Art

In general, administering medicine into the lungs of an asthma patient or the like is carried out, for example, by a method to inject the medicine into the patient, where the patient inhales the medicine by using a liquid aerosol sprayer, or where the patient inhales fine and granular medicine (having a grain size, for example, ranging from 5 to 10 μm) filled in a capsule upon breaking the capsule. Of these medicine administration methods, the method where the patient inhales fine and granular medicine involves inhaling medicine filled in a capsule upon breaking the capsule. Medicine in an amount corresponding to a plurality of doses is accommodated in a medicine administering apparatus, from which medicine in an amount corresponding to one dose is measured and taken out to be administered to the patient.

Another manner of administering the medicine to the patient is, for example, employed in a medicine administering apparatus disclosed in Japanese Patent Publication (Tokuhyohei) 3-504457. This medicine administering apparatus includes a disc-shaped administering unit formed with a plurality of administering holes. The administering unit is located at the bottom section of a material accommodating container in which powder material such as medicine or the like is accommodated, so that each administering hole of the administering unit is loaded with the material. A scraper is disposed in contact with the upper surface of the administering unit. The scraper scrapes an excessive portion of the material projected above each administering hole by rotating the administering unit.

In order to carry out medicine administration using this medicine administering apparatus, first the medicine as the powder material is accommodated within the material accommodating container, and then the medicine is dropped into each administering hole of the administering unit. Thereafter, an excess amount of the medicine projected above each administering hole is scraped by the scraper, thereby measuring and distributing the medicine in an amount corresponding to one dose. In this state, a patient holds the mouth piece of the medicine administering apparatus in his or her mouth and inhales the distributed medicine through the mouth piece. A medicine administering apparatus as disclosed in Japanese Patent Publication No. 1-47190 is constructed and arranged similarly to that discussed above and disclosed in Japanese Patent Publication No. 3-504457.

Additionally, the above method of medicine administration, where medicine in an amount corresponding to one dose is measured and taken out from in an amount of medicine corresponding to the plural doses, is used in a medicine administering apparatus disclosed in Japanese Patent Provisional Publication No. 59-88158. This medicine administering apparatus includes a blister case having a plurality of blisters which are circularly arranged. Each blister contains medicine corresponding to one dose and is adapted to be opened when each dose is to be made, so that the medicine in the blister is inhaled by a patient.

The above-discussed conventional medicine administering apparatuses are arranged such that medicine is dropped into an administering hole or the like under gravity, thereby distributing the medicine in the amount corresponding to one dose. Accordingly, the medicine administering apparatus uses a predetermined vertical locational relationship, so that the medicine cannot be accurately distributed when the medicine administering apparatus is in an inclined state. This requires the patient to raise up during medicine administration, thereby rendering medicine administration troublesome.

Of the above conventional medicine administering apparatuses, ones disclosed in Japanese Patent Publication No. 3-504457 and Japanese Patent Publication No. 1-47190 are arranged such that the medicine is dropped into each medicine administering hole and followed by scraping the excess medicine. However, there is the possibility that granular medicine partly cakes owing to humidity or the like, so that a difference in density occurs between a caked part and a granular part in the medicine. As a result, even though the medicine is distributed for each dose in the same way, a difference in actual amount of the medicine unavoidably occurs among respective portions distributed to be dosed. This makes it impossible to administer a predetermined amount of the medicine to the patient.

Difficulties have also been encountered in the above-discussed conventional medicine administering apparatus disclosed in Japanese Patent Provisional Publication No. 59-88158, in which the blister case has a plurality of the blisters for a plurality of doses. That is, the number of the blisters formed in the blister case is limited, and therefore a spare blister case is required to be carried by a patient.

SUMMARY OF THE INVENTION

It is an object of the present invention to provide an improved medicine administering apparatus which effectively overcomes drawbacks encountered in conventional medicine administering apparatuses.

Another object of the present invention is to provide an improved medicine administering apparatus which is largely facilitated in its handling or operability, while being improved in medicine administering efficiency.

A further object of the present invention is to provide an improved medicine administering apparatus which has no directional restriction during use, while making it possible to securely distribute a predetermined amount of medicine to be administered at each dose.

A medicine administering apparatus of the present invention comprises a main body which has a medicine loading chamber, and a medicine passage. The location of the medicine loading chamber is changed between a first position where the medicine loading chamber is separate from the medicine passage and a second position where the medicine loading chamber is in the medicine passage. A predetermined amount of medicine is loaded in a compressed state into the medicine loading chamber at the first position, the predetermined amount corresponding to one dose. The medicine within the medicine loading chamber is supplied through the medicine passage to a patient.

With this arrangement, the medicine in an amount corresponding to one dose is loaded in the compressed state into the medicine loading chamber of the main body of the medicine administering apparatus, and therefore the loaded medicine is caked in the medicine loading chamber so that the medicine in the medicine loading chamber can always be of a constant density. Accordingly, the medicine can be loaded into the medicine loading hole regardless of inclination or directional relationship of the medicine administering apparatus, thereby omitting a directional restriction of the medicine administering apparatus during use. Thus, the medicine administering apparatus can be largely improved in operability. Additionally, by changing the location of the medicine loading chamber into the medicine passage, medicine in an amount corresponding to one dose can be administered to the patient, thereby dosing a predetermined amount of the medicine to the patient, and improving the effects of the medicine. As discussed above, the medicine is loaded in its caked state in the medicine loading hole, and therefore the medicine can be easily administered to the patient lying in a bed without requiring the patient to raise his or her body during medicine administration.

BRIEF DESCRIPTION OF THE DRAWINGS

In the drawings, the same reference numerals designate same parts and elements throughout all figures.

DETAILED DESCRIPTION OF THE INVENTION

Figure 1:
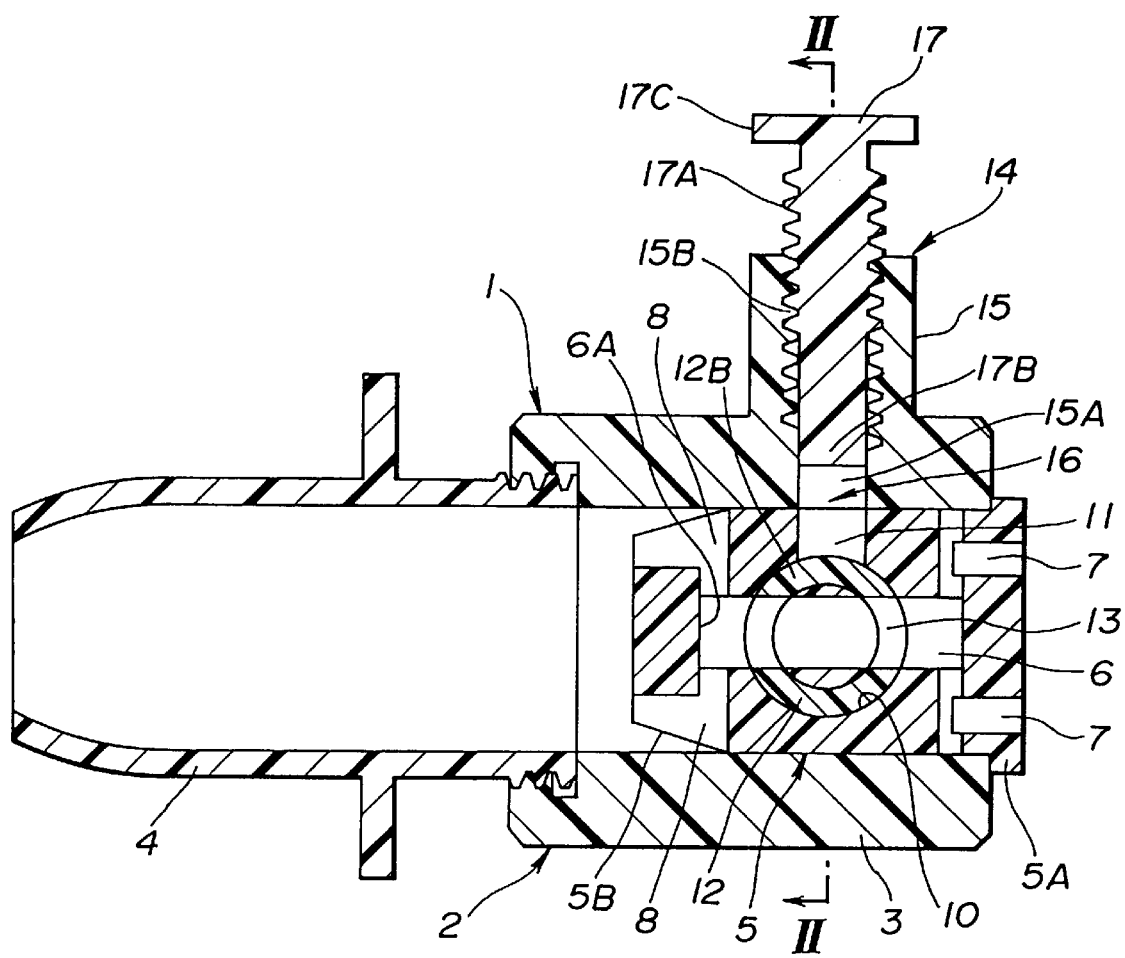
FIG. 1 is a vertical sectional view of a first embodiment of a medicine administering apparatus according to the present invention.
Figure 2:
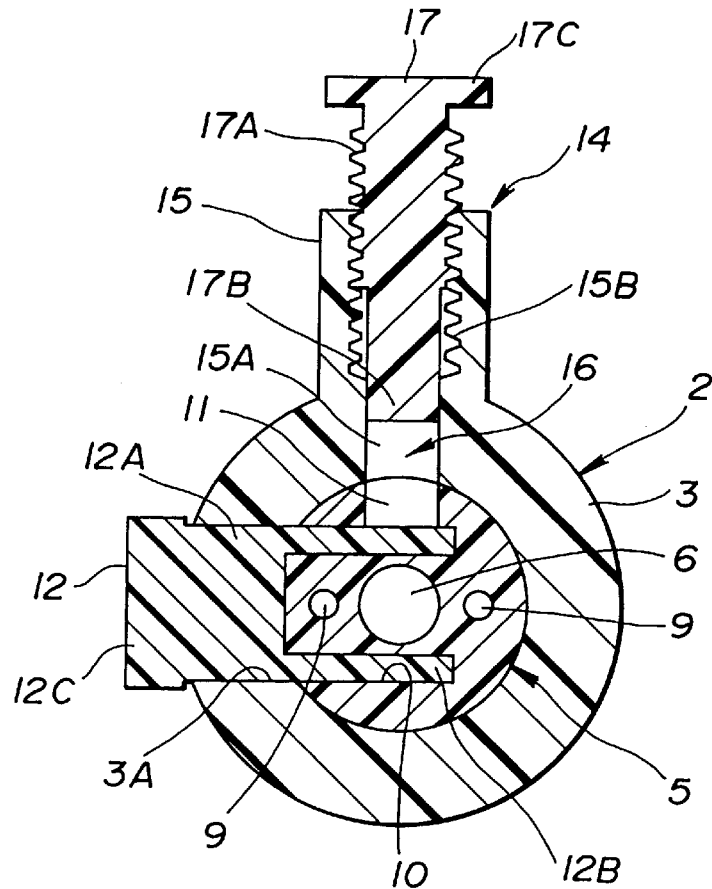
FIG. 2 is a sectional view taken in the direction of arrows substantially along the line II—II of FIG. 1.
Figure 3:
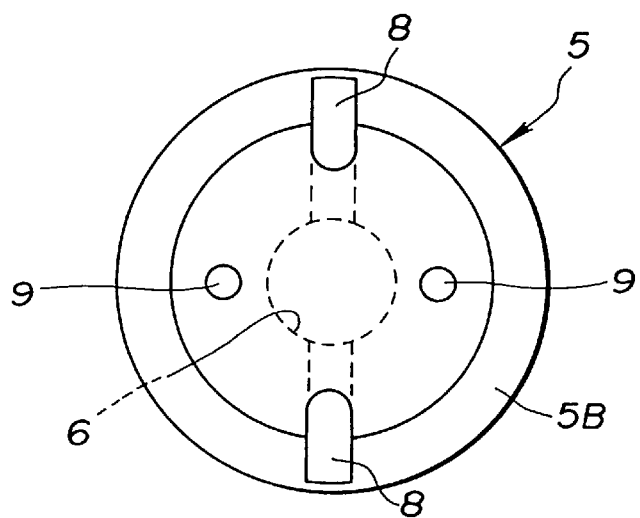
FIG. 3 is an enlarged left-side view of a passage member in the medicine administering apparatus of FIG. 1.

Referring now to FIGS. 1 to 6, and more specifically to FIGS. 1 to 3, of the drawings, a first embodiment of a medicine administering apparatus according to the present invention is illustrated by the reference numeral 1. The medicine administering apparatus 1 comprises a main body 2 which includes a generally cylindrical inhaling body 3 in which a passage member 5 is fitted. A mouth piece 4 is detachably threadedly connected to inhaling body 3. A hopper 15 (discussed after) is formed integrally with the inhaling body 3 to project radially outwardly from the outer peripheral surface of the inhaling body 3. The inhaling body 3 is formed with a fitting hole 3A which is located at a position separate 90 degrees from the hopper 15 in a peripheral direction of the inhaling body 3. The fitting hole 3A is formed piercing the cylindrical wall of the inhaling body 3 so as to be opened at the outer peripheral surface of the inhaling body 3. A change-over cylindrical member 12 is rotatably supported within the fitting hole 3A.

The passage member 5 is disposed within the inhaling body 3 and formed generally column-shaped. The passage member 5 is integrally formed at the outer periphery of its one end with an annular stopper section 5A which functions to locate the passage member 5 in the suction body 3 upon being brought into contact with one end of the inhaling body 3. The other end of the passage member 5 is formed in a generally frustoconical shape so as to have a tapered surface 5B whose diameter gradually decreases in a direction away from the annular stopper section 5A.

A medicine passage 6 is formed coaxial with the passage member 5 and extends along the center axis of the passage member 5. As shown in FIG. 1, the medicine passage 6 extends from the wall of the one end portion of the passage member 5 to the wall of the other end portion of the passage member 5. The one end portion of the passage member 5 is formed with two air inflow-side passages 7 which are located at the diametrically opposite sides of and communicated with the medicine passage 6. The other end portion of the passage member 5 is formed with two outflow-side passages 8 which are opened to the tapered surface 5B. The outflow-side passages 8 are formed by cutting out the frustoconical end portion of the passage member 5 through the tapered surface 5B. The outflow-side passages 8 are located at the diametrically opposite sides of and communicated with the medicine passage 6.

Thus, the inflow-side passage 7 is formed such that air is flown into the medicine passage 6 from the diametrically opposite outsides to generate two opposite air streams which strike against each other in the medicine passage 6, thereby producing a turbulence flow of air in the medicine passage 6. As a result, granular medicine in the medicine passage 6 can be effectively dispersed. Additionally, the wall of the other end portion of the passage member 5 serves as a medicine striking surface 6A to which the dispersed medicine strikes upon being carried by air stream flowing through the medicine passage 6, so that the medicine can be further finely pulverized.

The passage member 5 is further formed with two auxiliary air flow passages 9, which are formed at the diametrically opposite sides of the medicine passage 6. Each auxiliary air flow passage 9 is located at a 90 degree angle from each inflow-side passage 7 or outflow-side passage 8 in a peripheral direction of the passage member 5. Each auxiliary air flow passage 9 axially pierces the passage member 5 so as to extend from the tip end surface of the one end portion to the tip end surface of the other end portion of the passage member 5 in order to increase the amount of air to be sucked to a patient or user when the patient breathes in through the medicine administering apparatus 1, thereby avoiding any difficulty in breathing.

An annular groove 10 is formed in the passage member 5 which diametrically extends so that one end thereof is opened to the outer peripheral surface of the passage member 5, while the other end thereof is positioned in the solid part of the passage member 5 so as not to reach the outer peripheral surface of the passage member 5. The annular groove 10 extends across the medicine passage 6 and one (at the left side in FIG. 2) of the auxiliary air flow passage 9, and is located in such a manner that the axis of the annular groove 10 is perpendicular to that of the medicine passage 5. The annular groove 10 is coaxial with a cylindrical insertion hole 3A formed through the cylindrical wall of the inhaling body 3. The insertion hole 3A is coaxial with the annular groove 10 and formed in axial coincidence with each other.

A medicine accommodating hole 11 is formed in the passage member 5 to radially extend so that one end thereof is opened to the outer peripheral surface of the passage member 5, while the other end thereof is opened to the annular groove 10. The medicine accommodating hole 11 is located such that the extension of the axis thereof is perpendicular to the axis of the medicine passage 6. The medicine accommodating hole 11 has the same diameter as the medicine passage 6. The medicine accommodating hole 11 is further coincident with a medicine accommodating hole 15A formed in the inhaling body 3 to constitute a medicine accommodating chamber 16, in which the medicine accommodating hole 15A has the same diameter as the medicine accommodating hole 11. Medicine in an amount corresponding to a plurality of doses is accommodated in the medicine accommodating chamber 16.

The change-over cylindrical member 12 is disposed through the insertion hole 3A of the inhaling body 3 and the annular groove 10 of the passage member 5. The change-over cylindrical member 12 includes a cylindrical solid section 12A disposed within the insertion hole 3A of the inhaling body 3, and a cylindrical section 12B which coaxially extends from the solid section 12A and is rotatably fitted in the annular groove 10, maintaining a granule or powder tight seal. The solid section 12A has a dial portion 12C which is projected out of the insertion hole 3A of the inhaling body 3, so that the change-over cylindrical member 12 is rotationally operated upon being rotated through the dial portion 12C by the patient or user.

Two medicine loading holes (chambers) 13 are formed through the cylindrical wall of the cylindrical section 12B of the change-over cylindrical member 12. The two medicine loading holes 13 are located at the opposite sides of the axis of the cylindrical section 12B and be able to be brought into coincidence with the medicine passage 6 and with the medicine accommodating hole 11 by rotating the dial portion 12C of the change-over cylindrical member 12 by 90 degrees in angle. Thus, the rotational position of the medicine loading hole 13 can be changed by rotating the dial portion 12C so as to change the communication between the medicine loading hole 13 and the medicine accommodating hole 11 to the communication between the medicine loading hole 13 and the medicine passage 6 and vice versa. In other words, the medicine loading hole 13 can be selectively put into coincidence with the medicine accommodating hole 11 and the medicine passage 6. The medicine loading hole 13 has the same diameter as the medicine accommodating hole 11 and as the medicine passage 6. The volume of the medicine loading hole 13 defined between the inner and outer peripheral surfaces of the cylindrical section 12B of the change-over cylindrical member 12 is set to be loaded with the medicine (in a compressed state) in a predetermined volume required for each dose.

A medicine stuffing mechanism 14 is provided in the medicine administering apparatus 1 to stuff or compressedly load the medicine into the medicine accommodating chamber 16. The medicine stuffing mechanism 14 includes the hopper 15 which generally cylindrical and integral with the inhaling body 3. The hopper 15 projects radially outwardly to have a tip end separate from the inhaling body 3. The hopper 15 is formed at its most inner surface with an internal thread 17A. The inner peripheral surface defined by the internal thread 17A is aligned and communicated with the medicine accommodating hole 15A in the inhaling body 3.

A pusher 17 is formed generally column-like and includes a rod-like pushing section 17B which is formed at its outer peripheral surface with an external thread 17A engageable with the internal thread 15B of the hopper 15. A dial section 17C is formed at one end of the pushing section 17B which end is projected from the tip end of the hopper 15. The pushing section 17B is screwed in the axial hole of the hopper 15 by turning the dial section 17C, in which the medicine within the medicine accommodating chamber 16 is stuffed and compressed by the tip end of the pushing section 17B.

Figure 4:
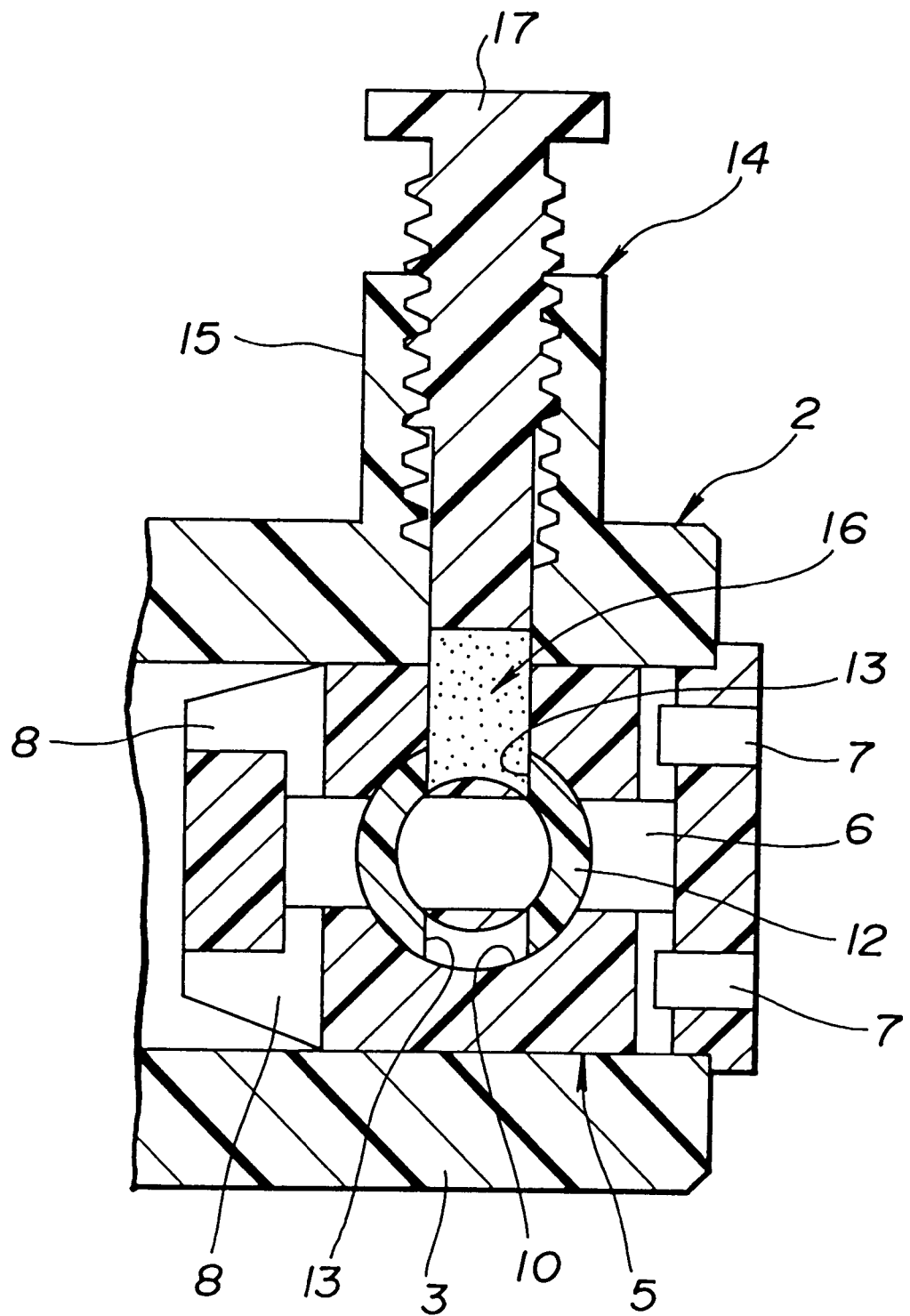
FIG. 4 is a fragmentary enlarged vertical sectional view of an essential part of the medicine administering apparatus of FIG. 1, showing an operational state in which medicine is forcibly loaded into a medicine loading hole at a medicine loading position under the action of a medicine stuffing mechanism.

Next, the manner of operation of the above medicine administering apparatus 1 will be discussed with reference to particularly FIGS. 4 to 6.

First, the change-over cylindrical member 12 is turned by turning its dial portion 12C so as to allow either one of the medicine loading holes 13 in the change-over cylindrical member 12 to come into coincidence (communication) with the medicine accommodating chamber 16, i.e., to come into a medicine loading position where the medicine is stuffed or loaded into the medicine loading hole 13. In this state, the pusher 17 is turned by a predetermined rotational angle, so that the granular medicine in an amount corresponding to one dose is stuffed or loaded in the medicine loading hole 13 in the change-over cylindrical member 12 as shown in FIG. 4. The medicine has been already stuffed in the medicine accommodating chamber 16 under the action of the pusher 17.

Figure 5:
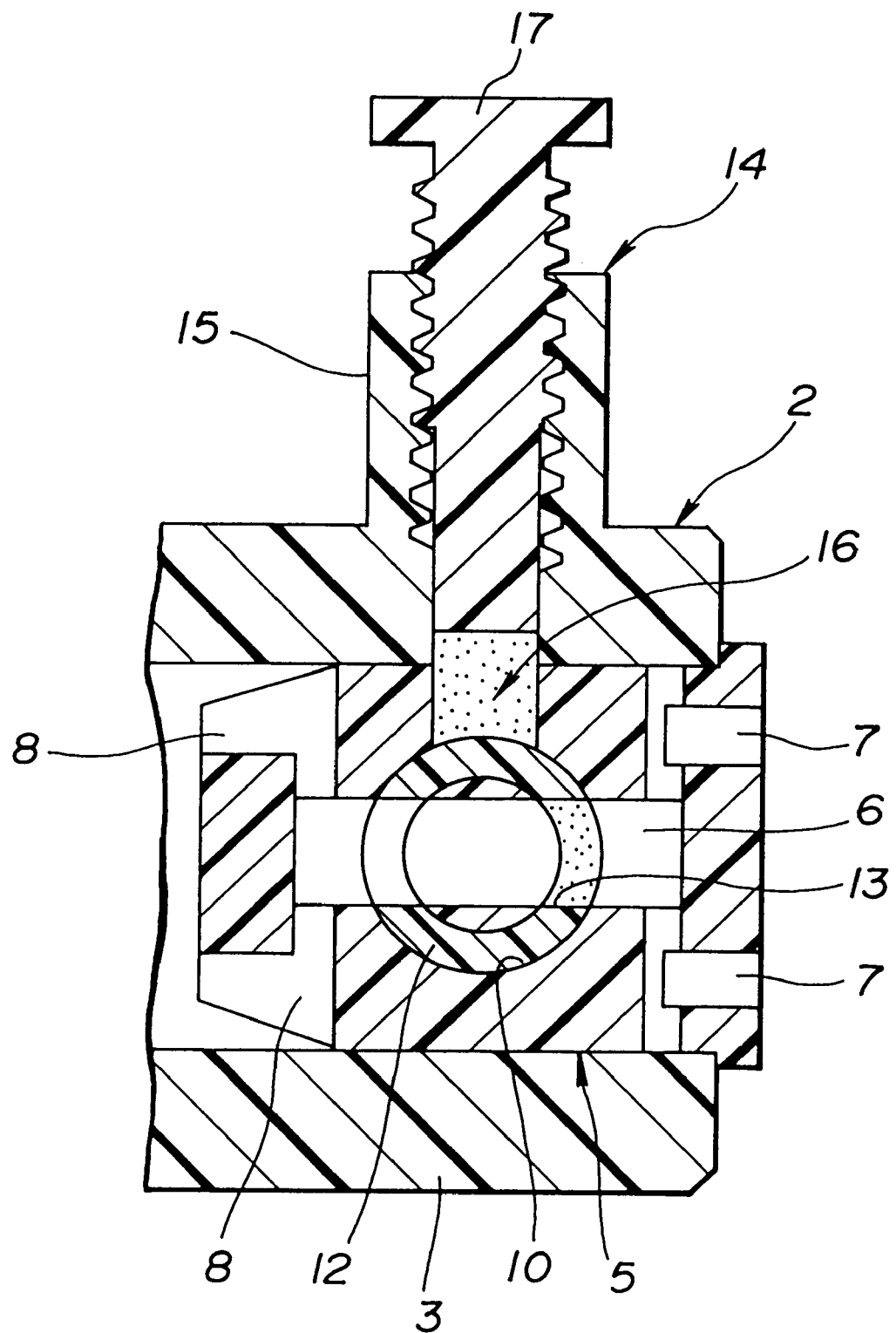
FIG. 5 is a fragmentary enlarged vertical sectional view similar to FIG. 4 but showing another operational state in which the medicine loading hole in the state of FIG. 4 is changed into a medicine administering position.

Upon completion of loading the medicine in the amount corresponding to one dose, the change-over cylindrical member 12 is turned right by a rotational angle of 90 degrees, so that the medicine loading hole 13 is located to come into coincidence with the medicine passage 6, i.e., to come into a medicine administering position where administration of the medicine is made, as shown in FIG. 5. At this time, the cylindrical section 12B of the change-over cylindrical member 12 is fitted in the annular groove 10 maintaining the powder tight seal, and therefore the medicine overflowing from the medicine loading hole 13 is scraped at the outer peripheral surface of the annular groove 10 when the medicine loading hole 13 is changed from the medicine loading position to the medicine administering position. As a result, the medicine in the amount corresponding securely to one dose can be measured and distributed to the side of the medicine passage 6.

Figure 6:
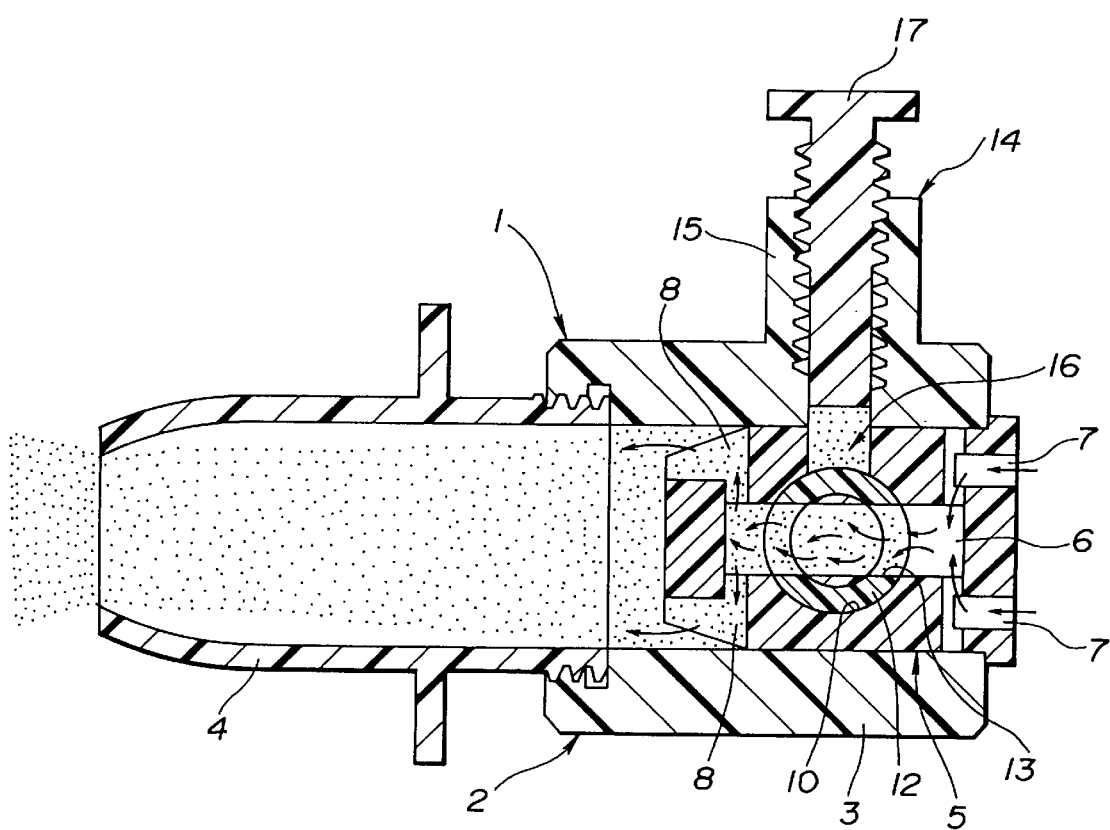
FIG. 6 is a vertical sectional view similar to FIG. 1 but showing an operational state of the medicine administering apparatus of FIG. 1, in which the medicine in the medicine loading hole at the medicine administering position of FIG. 5 is inhaled.
Figure 7:
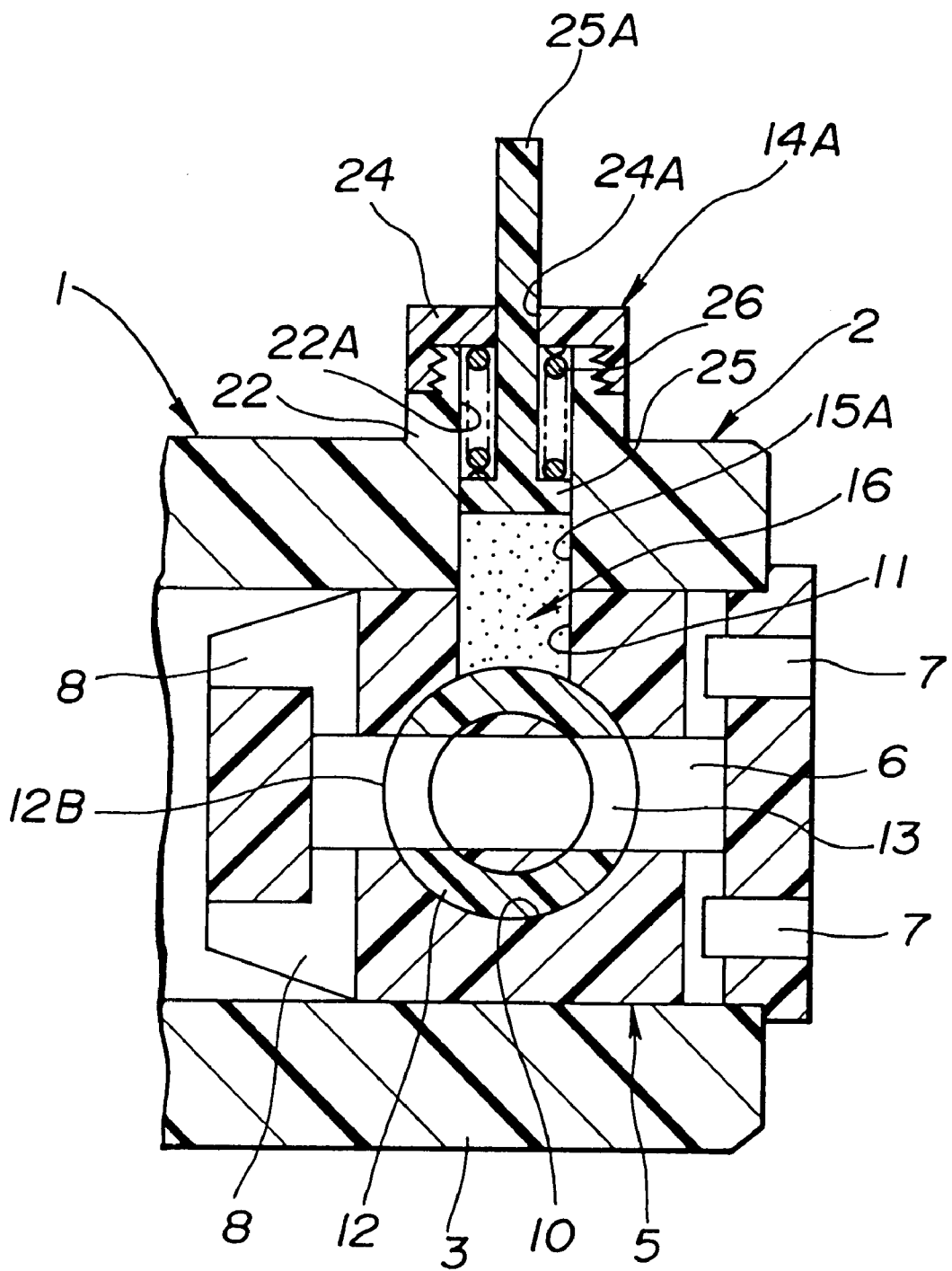
FIG. 7 is a fragmentary enlarged vertical sectional view of an essential part of a second embodiment of the medicine administering apparatus according to the present invention.

After the above preparation operation has been completed, the patient holds the mouth piece 4 in the mouth and breathes in, so that air flows through the inflow-side passages 7 into the medicine passage 6 as shown in FIG. 6. Then, the granular medicine filled in the medicine loading hole 13 of the cylindrical section 12B of the change-over cylindrical member 12 is dispersed to form an air stream mixing with the medicine. At this time, two air streams flow into the medicine passage 6 from opposite (radially inward) directions, and therefore the turbulence flow of air is generated within the medicine passage 6 thereby effectively dispersing the granular medicine. Additionally, the thus dispersed medicine flows axially and strikes against the medicine striking surface 6A, so that even a part of the medicine which has been left in an aggregate state can be securely finely pulverized to be effectively dispersed in air stream.

Air stream containing the medicine is released through the outflow-side passages 8 into the inside of the mouth piece 4 as shown in FIG. 6, and then reaches the inside of the lungs through the inside of the mouth and the trachea of the patient. Thus, the medicine in air stream can be administered to the lungs of the patient.

Figure 8:
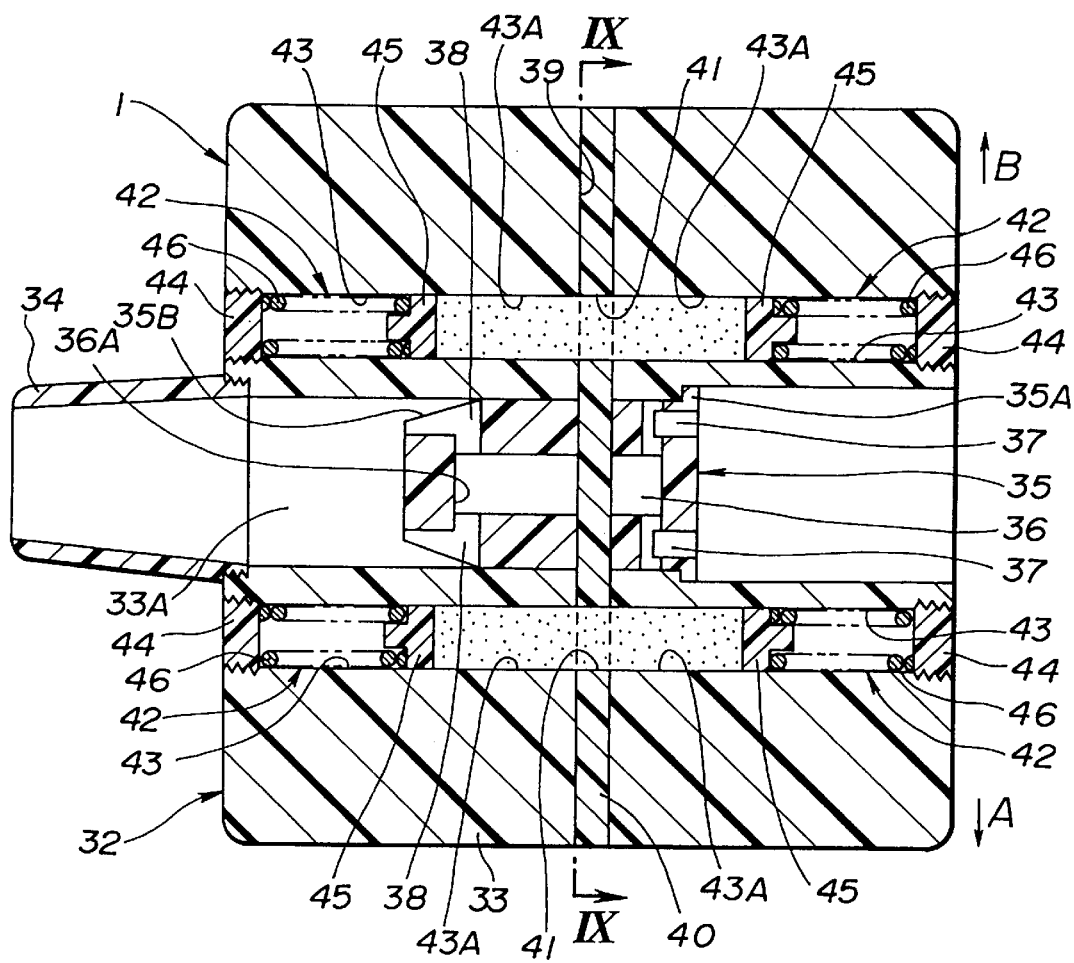
FIG. 8 is a vertical sectional view of a third embodiment of the medicine administering apparatus according to the present invention.

When the next medicine administration operation is to be made, the change-over cylindrical member 12 is turned 90 degrees in rotational angle to restore the medicine loading hole 13 to the medicine loading position, in which the above operations made after the medicine loading operation is to be repeated thereby repeatedly accomplishing administration of the medicine in the measured amount. Thus, a plurality of doses of the medicine are achieved.

Advantageous effects of the medicine administering apparatus of this embodiment will be discussed.

According to this embodiment, medicine within the medicine accommodating chamber 16 is compressed to a predetermined density under the action of the pusher 17 and then loaded into the medicine loading hole 13, and therefore the medicine can be loaded into the medicine loading hole 13 for the purpose of distributing the medicine in the amount corresponding to one dose even when the medicine stuffing mechanism 14 is located at the lower side of the medicine loading hole 13. This makes it possible to operate the medicine administering apparatus 1 in any direction, thereby greatly improving the operability of the medicine administering apparatus 1.

Additionally, since the medicine is loaded in its compressed state into the medicine loading hole 13 so as to keep the medicine in a lumped state in the medicine loading hole 13, it is possible to administer the medicine even where the medicine administering apparatus 1 is kept in a position where the axis of the main body 2 is vertical so that the mouth piece 4 is located below. This makes it possible to readily administer medicine even where the patient lies in a bed without raising up.

Further, medicine in the amount corresponding to one dose is loaded into the medicine loading hole 13 where the whole medicine has been stuffed to obtain a predetermined density. As a result, the amount of medicine for each dose can be prevented from being non-uniform due to difference in density, thereby facilitating administration of a predetermined amount of the medicine to the patient and raising the effects of the medicine.

Furthermore, medicine overflowing the medicine loading hole 13 can be scraped at the outer peripheral surface of the annular groove 10 when the medicine loading hole 13 is changed from the medicine loading position to the medicine administering position. Consequently, medicine in an amount corresponding to one dose can be measured and distributed to the side of the medicine passage 6 in the passage member 5, thus improving an administering efficiency.

Further, according to the medicine administering apparatus of this embodiment, the medicine loading hole 13 can be loaded from the medicine loading position to the medicine administering position or vice versa under the turning action of the change-over cylindrical member 12. This minimizes the space necessary to accomplish the change between the above two positions, thereby making the medicine administering apparatus small-sized.

FIG. 7 illustrates a second embodiment of the medicine administering apparatus 1 according to the present invention, which is similar to the first embodiment medicine administering apparatus 1, except that a medicine stuffing mechanism 14A is used in place of the medicine stuffing mechanism 14 of the first embodiment. The medicine stuffing mechanism 14A includes a generally cylindrical hopper 22 which is integral with the inhaling body 3 and projects radially outwardly from the outer peripheral surface of the inhaling body 3. The hopper 22 is formed with an axial central bore 22A which is aligned with and has the same diameter as the medicine accommodating chamber 16.

A cap 24 is threadedly attached to the tip end of the hopper 22 and formed with a central guide hole 24A. A piston 25 is movably disposed within the bore 22A of the hopper 22 and is insertable into the medicine accommodating chamber 16. The piston 25 is fixedly provided with a piston rod 25A which extends out of the cap 24 through the guide hole 24A. The piston 25 is movable in the axial direction of the medicine accommodating chamber 16 by moving the piston rod 25A. A spring member 26 is disposed within the axial bore 22A and located between the piston 25 and the cap 24. The biasing force of the spring member 26 is set at such a value as to obtain a predetermined density of the granular medicine within the medicine accommodating chamber 16.

With the above arrangement of this embodiment, first the medicine in an amount corresponding to a plurality of doses is supplied through the central bore 22A into the medicine accommodating chamber 16, and then the piston 25 is inserted into the central bore 22A by pushing the piston rod 25A. Thereafter, the spring member 26 and the cap 24 are successively assembled in position, in which the piston 25 is biased to push the medicine in the central bore 22A into the medicine accommodating chamber 16 so that the medicine is compressed to obtain a predetermined density. The thus compressed medicine is loaded into the medicine loading hole 13 formed in the cylindrical section 12B of the change-over cylindrical member 12.

According to this embodiment, generally the same advantageous effects as the first embodiment can be attained. Besides, the medicine within the medicine accommodating chamber 23 is compressed under the biasing force of the spring member 26, and therefore the operations of compressing the medicine and loading the medicine into the medicine loading hole 13 can be automatically accomplished, thereby improving the operability of the medicine administering apparatus 1.

FIGS. 8 to 11 illustrate a third embodiment of the medicine administering apparatus 1 according to the present invention, which is similar to the first embodiment of FIGS. 1 to 6. In this embodiment, the medicine administering apparatus 1 comprises a main body 32 which includes an inhaling body 33 formed into the shape of a rectangular plate having a considerable thickness. The inhaling body 33 is formed with an installation through-hole 33A which is located at the central part of the inhaling body 33 and extends from one end to the other end of the inhaling body 33 to which end a mouth piece 34 is threadedly connected.

A passage member 35 is fitted in the installation through-hole 33A and formed generally column-shaped. The passage member 5 is integrally formed at the outer periphery of its one end with an annular stopper section 35A which functions to locate the passage member 35 to the installation through-hole upon being brought into contact with a step portion (not identified) formed in the installation through-hole 33A. The other end of the passage member 35 is formed in a generally frustoconical shape so as to have a tapered surface 35B whose diameter gradually decreases in a direction away from the annular stopper section 35A.

A medicine passage 36 is formed coaxial with the passage member 35 and extends along the center axis of the passage member 35. As shown in FIG. 8, the medicine passage 36 extends from the wall of the one end portion of the passage member 35 to the wall of the other end portion of the passage member 35. The one end portion of the passage member 35 is formed with two air inflow-side passages 37 which are located at the diametrically opposite sides of and communicated with the medicine passage 36. The other end portion of the passage member 35 is formed with two outflow-side passages 8 which are opened to the tapered surface 35B. The outflow-side passages 38 are formed by cutting out the frustoconical end portion of the passage member 35 through the tapered surface 35B. The outflow-side passages 38 are located at the diametrically opposite sides of and communicated with the medicine passage 36.

Figure 9:
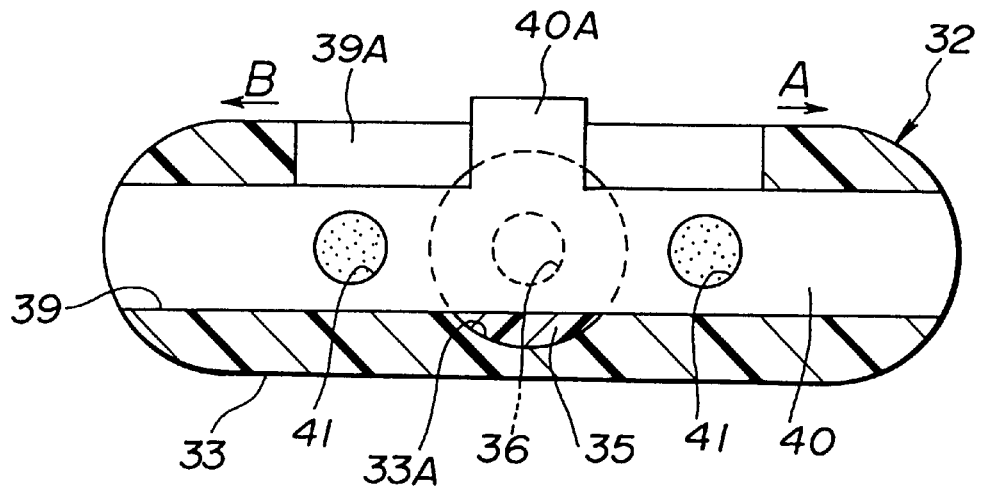
FIG. 9 is a sectional view taken in the direction of arrows IX—IX of FIG. 8, showing an operational state of the medicine administering apparatus.

A sliding hole 39 is formed piercing the inhaling body 33 and is located perpendicular to the installation through-hole 33A. The sliding hole 39 is rectangular in section and contiguous with a central groove 39A opened to the central part of the flat surface of the inhaling body 33, as shown in FIG. 9. A flat change-over plate member 40 is disposed within the sliding hole 39 to be slidable in directions indicated by arrows A and B in FIG. 9. The change-over plate member 40 is integrally formed at its central part with an operation projection 40A which is slidably disposed in the central groove 39A and projects out of the inhaling body 33.

Figure 10:
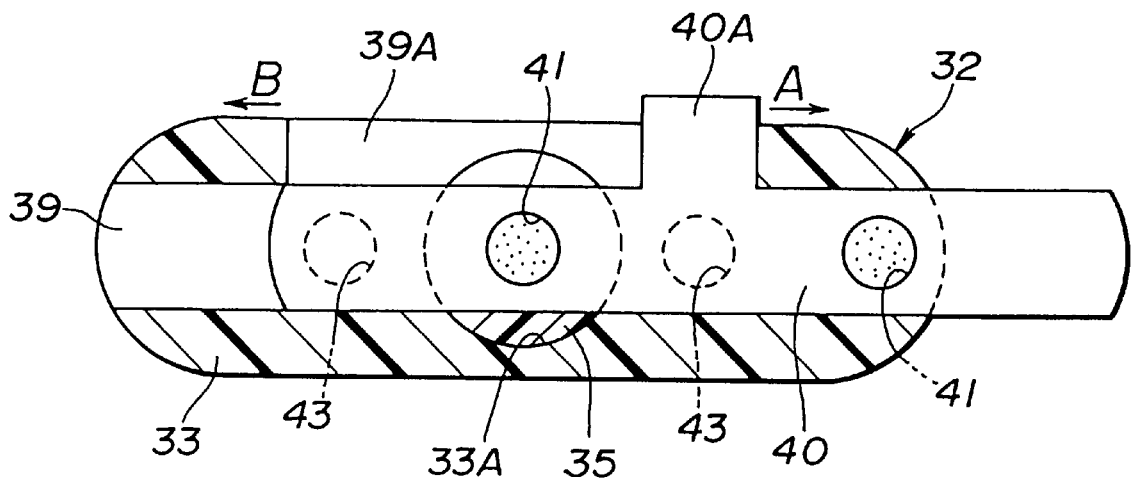
FIG. 10 is a sectional view similar to FIG. 9 but showing another operational state of the medicine administering apparatus.

The change-over plate member 40 is formed with two medicine loading holes 41, each of which has the same diameter as the medicine passage 36 and has such a volume so as to be loaded with medicine in an amount necessary for one dose. The medicine loading holes 41 are arranged and located such that either one of the two medicine loading holes 41 comes into coincidence (communication) with the medicine passage 36, while the other cannot come out of the sliding hole 39 when the operation projection 40A is moved by the patient or user in the direction of the arrow A or B in FIG. 9 until the operation projection 40A comes into contact with one of the opposite ends of the central groove 39A. In this connection, FIG. 10 shows a state in which the operation projection 40A is moved in the direction of the arrow A.

Four medicine stuffing mechanisms 42 are disposed in the inhaling body 33 and in parallel with the installation through-hole 33A to stuff or load the medicine into the medicine loading holes 41. A first pair of the medicine stuffing mechanisms 42 (shown above the installation through-hole 33A in FIG. 8) is located at the opposite sides of the change-over plate member 40, in which the mechanisms 42 are coaxial and aligned with each other. A second pair of the medicine stuffing mechanisms 42 is located at the opposite sides of the change-over plate member 40, in which the mechanisms 42 are coaxial and aligned with each other. The first and second pairs of the medicine stuffing mechanisms 42 are generally symmetrical with respect to and located at the opposite sides of the installation through-holes 33A.

Each of the first pair of the medicine stuffing mechanisms 42 includes a piston 45 slidably disposed in a straight through-hole 43 which extends through the sliding hole 39. The pistons 45 of the first pair of the medicine stuffing mechanisms 42 are located facing each other and at the opposite sides of the sliding hole 39 to define therebetween two medicine accommodating chambers 43A. The two medicine accommodating chambers 43A are coaxial and aligned with each other so as to be contiguous with each other through the sliding hole 39. It will be understood that the two medicine accommodating chambers 43A form part of the through-hole 43. Each medicine accommodating chamber 43A has the same diameter as the medicine passage 36 and as each medicine loading hole 41. Each medicine accommodating chamber 43A is to contain therein the medicine in an amount corresponding to a plurality of doses.

A pair of caps 44 are screwed respectively at the opposite end portions of the through-hole 43. A spring member 46 is disposed between each piston and the corresponding cap 44. The biasing force of each spring member 46 is set such that the granular medicine is compressed to have a predetermined density when the piston 45 pushes the medicine within the medicine accommodating chamber 43.

It will be appreciated that a second pair of the medicine stuffing mechanisms 42 (shown below the installation through-hole 33A in FIG. 8) are constructed and arranged in the same manner as that in the first pair of the medicine stuffing mechanisms 42. Accordingly, each medicine accommodating chamber 43 of the first pair of the medicine stuffing mechanisms 42 and each medicine accommodating chamber 43 of the second pair of the medicine stuffing mechanisms 42 are arranged to have the same distance as that of the two medicine loading holes 41 in the change-over plate member 40, and therefore to be capable of being coincident respectively with the medicine loading holes 41. It will be understood that each medicine loading hole 41 is capable of being brought into coincidence with the medicine passage 36 of the passage member 35.

Here, each medicine stuffing mechanism 42 is assembled as follows: After medicine in the amount corresponding to plural doses is supplied into the medicine accommodating chamber 43, the piston 45 is inserted into the through-hole 43. Then, the spring member 46 and the cap 44 are successively assembled, so that the piston 45 compresses the medicine within the medicine accommodating chamber 43 under the biasing force of the spring member 46. Accordingly, the medicine is loaded into each medicine loading hole 41 under a state in which the medicine has been compressed to have a predetermined density.

In operation, where the change-over plate member 40 is located at a neutral position as shown in FIGS. 8 and 9, the medicine loading holes 41 are respectively brought into coincidence (communication) with the medicine accommodating chambers 43A, i.e., into the medicine loading positions, so that each medicine loading hole 41 is loaded with the medicine which has been compressed to have the predetermined density.

Subsequently, the change-over plate member 40 is moved in the direction of the arrow A through the operation projection 40A as shown in FIG. 10, so that the medicine loading hole 41 (at the left side in FIGS. 9 and 10) is brought into coincidence with the medicine passage 36, i.e., into the medicine administering position. Here, since the change-over plate member 40 is slidably disposed or fitted in the sliding hole 39 in a manner to maintain a powder tight seal, the medicine overflowing the medicine loading hole 41 is scraped at the inner surface of the sliding hole 39 when each medicine loading hole 41 is changed from the medicine loading position to the medicine administering position. Accordingly, the medicine in the amount corresponding to one dose can be securely distributed into the medicine passage 36.

In order to put the medicine loading hole 41 (at the right side in FIG. 9) into the medicine loading position, the change-over plate member 40 is moved in the direction of the arrow B through the operation projection 40A so that the medicine loading hole 41 is brought into coincidence (communication) with the medicine passage 36.

Operations (flow of air and the medicine) of the medicine administering apparatus 1 of this embodiment during a time where the patient inhales the medicine are the same as those in the first embodiment of the medicine administering apparatus, and therefore explanation thereof is omitted for purpose of simplicity of illustration.

As appreciated from the above, according to this embodiment, medicine in the amount corresponding to one dose is forcibly loaded into each medicine loading hole 41 by the two medicine stuffing mechanisms 42, and therefore a large amount of the medicine can be stored in the four medicine accommodating chambers 43. This allows the medicine administering apparatus 1 to be used for a long time upon once-charging of the medicine into the four medicine accommodating chambers 43.

Additionally, the pair of the medicine stuffing mechanisms 42 (including the medicine accommodating chambers 43) are arranged at the opposite sides of the change-over plate member 40 (having each medicine loading hole 41), and therefore the medicine administering apparatus may be made compact or small-sized.

Further, in this embodiment, different medicines may be supplied respectively to the medicine accommodating chambers 43 of the first pair of the medicine stuffing mechanisms 42 and the medicine accommodating chambers 43 of the second pair of the medicine stuffing mechanisms 42. This makes it possible to administer two kinds of medicines to a patient. By changing the diameter (or the volume) of each medicine loading hole 41, the amount of the medicine to be administered can be set according to the kind of medicine, while providing two kinds of medicine administering apparatuses, one of which is for an adult person and the other for a child.

While the four medicine stuffing mechanisms 42 have been shown and described as being provided in the third embodiment of the medicine administering apparatus, it will be appreciated that only two medicine stuffing mechanisms may be provided at one side of the change-over plate member 40 or respectively at the opposite side of the change-over plate member 40, or only one medicine stuffing mechanism may be provided at one side of the change-over plate member 40 or of the installation through-hole 33A.

Although the medicine administering apparatus of the first to third embodiments has been shown and described as being arranged such that medicine is inhaled upon being held in the mouth, it will be understood that the principle of the present invention may be applicable to other medicine administering apparatuses, such as one which is arranged such that medicine is inhaled through a nasal cavity of a patient.

What is claimed is:

1. A medicine administering apparatus comprising:
   a main body including a medicine passage and a medicine accommodating chamber;
   a location changing member for changing a location of a medicine loading chamber between a first position where said medicine loading chamber communicates with said medicine accommodating chamber and a second position where said medicine loading chamber forms part of said medicine passage so that air flowing through said medicine passage passes through said medicine loading chamber to supply medicine within said medicine passage to a patient; and
   a medicine loading portion for loading a predetermined amount of medicine into said medicine loading chamber when said medicine loading chamber is in the first position, said predetermined amount corresponding to one dose, said medicine loading portion having a medicine loading member movable in a direction toward an open end of said medicine loading chamber and adapted to compress medicine in said medicine accommodating chamber into a compressed state to load said predetermined amount in said medicine loading chamber.

2. A medicine administering apparatus as claimed in claim 1, wherein said medicine accommodating chamber accommodates a plurality of doses.

3. A medicine administering apparatus as claimed in claim 2, wherein said medicine loading member is a pushing member having a longitudinal axis, said pushing member being formed with an external thread and adapted to engage an internal thread formed in said medicine accommodating chamber of said main body, said pushing member being axially movable to compress the medicine in said medicine accommodating chamber upon being rotated about its longitudinal axis.

4. A medicine administering apparatus as claimed in claim 3, wherein said location changing member includes a cylindrical member rotatably supported in said main body and formed with a hole, said hole serving as said medicine loading chamber, and a location of said hole being changed between said first position where said hole is in communication with said medicine accommodating chamber and said second position where said hole is in communication with said medicine passage.

5. A medicine administering apparatus as claimed in claim 2, wherein said medicine loading member is a piston slidably disposed in said medicine accommodating chamber of said main body, and said medicine loading portion includes a spring for biasing said piston to compress the medicine within said medicine accommodating chamber.

6. A medicine administering apparatus as claimed in claim 2, wherein said location changing member includes a plate member slidably disposed in said main body and located generally perpendicular to said medicine passage, said plate member having a hole formed through a wall of said plate member, said hole serving as said medicine loading chamber, location of said hole being changed between a first position where said hole is in communication with said medicine accommodating chamber and a second position where said hole is in communication with said medicine passage.

7. A medicine administering apparatus as claimed in claim 6, wherein said medicine accommodating chamber extends generally perpendicular to said plate member and generally parallel with said medicine passage.

8. A medicine administering apparatus as claimed in claim 7, further comprising means defining a sliding hole formed in said main body, said sliding hole extending generally perpendicular to said medicine accommodating chamber and said medicine passage, said plate member being slidably fitted in said sliding hole.

9. A medicine administering apparatus as claimed in claim 8, wherein said medicine accommodating chamber comprises a first chamber and a second chamber, said first and second chambers located parallel to and on opposite sides of said medicine passage, said plate member being perpendicular to and intersecting said first and second chambers and said medicine passage.

10. A medicine administering apparatus as claimed in claim 9, further comprising a first medicine stuffing mechanism disposed at each end of said first chamber and a second medicine stuffing mechanism disposed at each end of said second chamber for compressing the medicine within the first chamber and the medicine within the second chamber respectively.

11. A medicine administering apparatus comprising:

a main body having a medicine passage and a groove that communicates with said medicine passage, a change-over member slidably fitted in said groove, and a medicine loading chamber formed in said change-over member;

means for moving said change-over member so as to change a location of said medicine loading chamber between a first position, where said medicine loading chamber communicates with a medicine accommodating chamber, and a second position, where said medicine loading chamber forms part of said medicine passage so that air flowing through said medicine passage passes through said medicine loading chamber to supply medicine within said medicine passage to a patient;

a medicine loading portion for loading a predetermined amount of medicine into said medicine loading chamber when said medicine loading chamber is in the first position, said predetermined amount corresponding to one dose; and a loading member movable in a direction toward an open end of said medicine loading chamber and adapted to compress the medicine into a compressed state to load said predetermined amount into said medicine loading chamber.

12. A medicine administering apparatus comprising:

a main body having a medicine passage and a groove that communicates with said medicine passage, a cylindrical change-over member slidably fitted in said groove, and a medicine loading chamber formed in said change-over member, said medicine loading chamber piercing a cylindrical wall of said change-over member;

means for moving said change-over member so as to change a location of said medicine loading chamber between a first position, where said medicine loading chamber communicates with a medicine accommodating chamber, and a second position, where said medicine loading chamber is in coincidence with said medicine passage and forms part of said medicine passage so that air flowing through said medicine passage passes through said medicine loading chamber to supply medicine to a patient;

a medicine loading portion for loading a predetermined amount of medicine into said medicine loading chamber when said medicine loading chamber is in the first position, said predetermined amount corresponding to one dose; and a loading member movable in a direction toward an open end of said medicine loading chamber and adapted to compress the medicine into a compressed state to load said predetermined amount into said medicine loading chamber.

* * * * *